(12) United States Patent
Rutan

(10) Patent No.: US 11,642,482 B2
(45) Date of Patent: May 9, 2023

(54) LINER AND RETAINING MEMBER FOR USE WITH RESPIRATORY MASK

(71) Applicant: Naturs Design, Inc., Jackson, MI (US)

(72) Inventor: Robert M. Rutan, Jackson, MI (US)

(73) Assignee: Naturs Design, Inc., Jackson, MI (US)

(*) Notice: Subject to any disclaimer, the term of this patent is extended or adjusted under 35 U.S.C. 154(b) by 1078 days.

(21) Appl. No.: 16/365,980

(22) Filed: Mar. 27, 2019

(65) Prior Publication Data

US 2019/0298955 A1 Oct. 3, 2019

Related U.S. Application Data

(60) Provisional application No. 62/648,895, filed on Mar. 27, 2018.

(51) Int. Cl.
*A61M 16/06* (2006.01)
*A62B 18/02* (2006.01)
(Continued)

(52) U.S. Cl.
CPC ....... *A61M 16/0616* (2014.02); *A62B 18/025* (2013.01); *A61B 5/097* (2013.01); *A61M 2205/0238* (2013.01); *A62B 23/025* (2013.01)

(58) Field of Classification Search
CPC .............. A61M 16/0616; A61M 16/06; A61M 16/0605; A61M 16/0611; A61M 16/0622;
(Continued)

(56) References Cited

U.S. PATENT DOCUMENTS

| 1,990,199 A | 2/1935 | Nemzek |
| 2,008,677 A | 7/1935 | Booharin |

(Continued)

FOREIGN PATENT DOCUMENTS

| CN | 1623609 A | 6/2005 |
| CN | 1681551 A | 10/2005 |

(Continued)

OTHER PUBLICATIONS www.cpaptalk.com, May 6, 2006—Nov. 30, 2005.
(Continued)

*Primary Examiner* — Joseph D. Boecker
*Assistant Examiner* — Brian T Khong
(74) *Attorney, Agent, or Firm* — Brooks Kushman P.C.

(57) ABSTRACT

A respiratory mask includes a mask body having a face-engaging portion, and at least one retaining member connected to the mask body and including at least one engaging member for receiving and tethering a liner to the respiratory mask to generally overlie the face-engaging portion. The retaining member may include a flexible elongated body having a central portion and opposing ends, and a bottom surface arranged to be attached to the respiratory mask. The liner may include a liner body constructed from an absorbent material and having an outer edge, an inner edge, and an opening bounded by the inner edge, wherein an extending portion of the liner body is defined which extends outwardly beyond the face-engaging portion and includes at least one aperture for engaging the retaining member. A kit for use with a respiratory mask includes at least one liner and at least one retaining member.

18 Claims, 8 Drawing Sheets

(51) Int. Cl.
*A62B 23/02* (2006.01)
*A61B 5/097* (2006.01)

(58) Field of Classification Search
CPC .......... A61M 16/0627; A61M 16/0633; A61M 16/0666; A61M 16/0683; A61M 2016/0661; A62B 18/02; A62B 18/025; A62B 18/084; A62B 23/025; A62B 23/02
See application file for complete search history.

(56) References Cited

U.S. PATENT DOCUMENTS

| | | |
|---|---|---|
| 2,435,721 A | 2/1948 | Lehmann |
| 2,931,356 A | 4/1960 | Schwarz |
| 3,130,722 A | 4/1964 | Dempsey et al. |
| 3,357,426 A | 12/1967 | Cohen |
| 4,069,516 A | 1/1978 | Watkins, Jr. |
| D257,063 S | 9/1980 | Galindo |
| 4,856,508 A | 8/1989 | Tayebi |
| 5,003,633 A | 4/1991 | Itoh |
| 5,146,914 A | 9/1992 | Sturrock |
| 5,243,971 A | 9/1993 | Sullivan et al. |
| 5,429,683 A | 7/1995 | Le Mitouard |
| 5,921,239 A | 7/1999 | McCall et al. |
| 6,016,805 A | 1/2000 | Burns et al. |
| 6,082,360 A | 7/2000 | Rudolph et al. |
| 6,196,223 B1 | 3/2001 | Belfer et al. |
| D442,352 S | 5/2001 | Benjamin et al. |
| 6,338,340 B1 | 1/2002 | Finch et al. |
| 6,468,222 B1 | 10/2002 | Mault et al. |
| 6,530,373 B1 | 3/2003 | Patron et al. |
| 6,629,531 B2 | 10/2003 | Gleason et al. |
| 6,698,427 B1 | 3/2004 | Clowers |
| 6,698,727 B1 | 3/2004 | Shaw |
| 6,851,429 B2 | 2/2005 | Bishop |
| 6,926,004 B2 | 8/2005 | Schumacher |
| 6,955,650 B2 | 10/2005 | Mault et al. |
| 7,000,614 B2 | 2/2006 | Lang et al. |
| 7,017,577 B2 | 3/2006 | Matich |
| 7,077,138 B2 | 7/2006 | Bateman et al. |
| 7,178,525 B2 | 2/2007 | Matula, Jr. et al. |
| 7,219,670 B2 | 5/2007 | Jones, Jr. et al. |
| 7,234,466 B2 | 6/2007 | Kwok et al. |
| 7,243,650 B2 | 7/2007 | Thornton |
| 7,296,574 B2 | 11/2007 | Ho et al. |
| 7,370,652 B2 | 5/2008 | Matula, Jr. et al. |
| 7,427,703 B2 | 9/2008 | Geier |
| D644,729 S | 9/2011 | Ferris et al. |
| 8,171,934 B1 | 5/2012 | Ho |
| 8,365,733 B2 | 2/2013 | Rutan |
| D717,939 S | 11/2014 | Koehler |
| D735,318 S | 7/2015 | Roblin-Lee |
| 9,113,667 B2 | 8/2015 | Rutan |
| D738,514 S | 9/2015 | Tagami et al. |
| D755,951 S | 5/2016 | Roblin-Sharp |
| 10,071,216 B2 | 9/2018 | Rutan |
| 10,357,626 B1* | 7/2019 | Baker ............... A61M 16/0057 |
| 2003/0023182 A1 | 1/2003 | Mault et al. |
| 2003/0075180 A1 | 4/2003 | Raje et al. |
| 2004/0078860 A1* | 4/2004 | Bell ................... A41D 13/1161 |
| | | 128/206.13 |
| 2004/0194784 A1 | 10/2004 | Bertrand |
| 2004/0244804 A1 | 12/2004 | Olsen et al. |
| 2004/0247479 A1 | 12/2004 | Landis |
| 2004/0261797 A1 | 12/2004 | White et al. |
| 2005/0199239 A1 | 9/2005 | Lang et al. |
| 2005/0268907 A1 | 12/2005 | McFarlane |
| 2005/0279367 A1 | 12/2005 | Klemperer |
| 2005/0284481 A1 | 12/2005 | Meyer et al. |
| 2006/0000476 A1* | 1/2006 | Salem ............... A61M 16/0683 |
| | | 128/207.11 |
| 2006/0060200 A1 | 3/2006 | Ho et al. |
| 2006/0081251 A1 | 4/2006 | Hernandez et al. |
| 2006/0107431 A1 | 5/2006 | Curran et al. |
| 2006/0130845 A1 | 6/2006 | Schegerin |
| 2006/0144399 A1 | 7/2006 | Davidowski et al. |
| 2006/0283452 A1 | 12/2006 | Woodard et al. |
| 2007/0006879 A1 | 1/2007 | Thornton |
| 2007/0017525 A1 | 1/2007 | Madaus et al. |
| 2007/0050883 A1 | 3/2007 | Matich |
| 2007/0157934 A1 | 7/2007 | Lang et al. |
| 2007/0175479 A1 | 8/2007 | Groll |
| 2007/0175480 A1 | 8/2007 | Gradon et al. |
| 2008/0047560 A1 | 2/2008 | Veliss et al. |
| 2008/0110469 A1 | 5/2008 | Weinberg |
| 2008/0127984 A1 | 6/2008 | Thornton |
| 2008/0257354 A1 | 10/2008 | Davidson et al. |
| 2008/0295845 A1* | 12/2008 | Nashed ............... A61M 16/085 |
| | | 128/206.26 |
| 2008/0302365 A1 | 12/2008 | Cohen et al. |
| 2009/0050144 A1 | 2/2009 | Pierce et al. |
| 2009/0107507 A1 | 4/2009 | Moore |
| 2009/0139525 A1 | 6/2009 | Schirm |
| 2009/0211581 A1 | 8/2009 | Bansal |
| 2010/0031958 A1 | 2/2010 | Stewart |
| 2010/0108072 A1* | 5/2010 | D'Souza ........... A61M 16/0616 |
| | | 128/206.24 |
| 2010/0326445 A1 | 12/2010 | Veliss et al. |
| 2011/0005524 A1 | 1/2011 | Veliss et al. |
| 2011/0061656 A1 | 3/2011 | Matich |
| 2011/0226240 A1 | 9/2011 | Navalesi et al. |
| 2012/0080035 A1 | 4/2012 | Guney et al. |
| 2012/0180794 A1 | 7/2012 | Smart |
| 2012/0180795 A1 | 7/2012 | Knight |
| 2012/0204881 A1* | 8/2012 | Davidson .......... A61M 16/0605 |
| | | 128/206.25 |
| 2013/0139290 A1 | 6/2013 | Barski |
| 2014/0150799 A1 | 6/2014 | Daly |
| 2014/0158137 A1 | 6/2014 | Ging et al. |
| 2014/0190492 A1 | 7/2014 | Noh et al. |
| 2014/0345621 A1 | 11/2014 | Zack et al. |
| 2015/0352307 A1* | 12/2015 | Rutan .................... A61B 5/097 |
| | | 128/206.24 |
| 2015/0352309 A1 | 12/2015 | Daly |
| 2015/0374943 A1 | 12/2015 | Alexani |
| 2015/0374945 A1 | 12/2015 | Anthony |
| 2016/0279359 A1 | 9/2016 | Chang et al. |
| 2016/0339196 A1 | 11/2016 | Bowsher |
| 2017/0049983 A1 | 2/2017 | Ellis |
| 2017/0361039 A1* | 12/2017 | Valentino ................. A41G 7/00 |
| 2019/0001093 A1 | 1/2019 | Rutan |

FOREIGN PATENT DOCUMENTS

| | | |
|---|---|---|
| CN | 1681553 A | 12/2005 |
| CN | 101653632 A | 2/2010 |
| CN | 102065786 A | 5/2011 |
| CN | 102448550 A | 5/2012 |
| GB | 162526 | 5/1921 |
| JP | 551364 U | 7/1993 |
| JP | 2000217940 A | 8/2000 |
| JP | 2003501220 A | 1/2003 |
| JP | 2003052845 A | 2/2003 |
| JP | 2005537904 A | 12/2005 |
| KR | 20100003822 A | 1/2010 |
| WO | 9925410 A1 | 5/1999 |
| WO | 0050121 A1 | 8/2000 |
| WO | 0076568 A1 | 12/2000 |
| WO | 2004022145 A1 | 3/2004 |
| WO | 2008011683 A1 | 1/2008 |
| WO | 2008137644 A1 | 11/2008 |
| WO | 2009146313 A1 | 12/2009 |
| WO | 2014120492 A1 | 8/2014 |

OTHER PUBLICATIONS

"Mirage Micro Nasal Mask", ResMed, 2007, from www.resmed.com.

(2006), CPAP Community—View Topic—Mask Gasket [Web log post]. Retrieved from http://www.cpaptalk.com/viewtopic.

(56) References Cited

OTHER PUBLICATIONS (2006), CPAP Community—View Topic—Mask Experiment Success [Web log post]. Retrieved from http://www.cpaptalk.com/viewtopic.
(2005-2011), CPAP Community—View Topic—Directions for Toilet Seat Covering [Web log post]. Retrieved from http://www.cpaptalk.com/viewtopic.
"Pad a Cheek", PAC_OptiLife, from http://www.padacheek.com/PAC_Maskliner.html, obtained from www.archive.org, published at least as early as Apr. 8, 2012.
(Nov. 22, 2007), CPAP Community, "Deconstructed Aura" [Web log post]. Retrieved from http://www.cpaptalk.com/viewtopic.
(2007), CPAP Community, "Decapitating a Twilite NP Mask" [Web log post]. Retrieved from http://cpaptalk.com/viewtopic.
(2007), CPAP Community, by Wulfman [Web log post]. Retrieved from http://cpaptalk.com/viewtopic.
(Nov. 30, 2007), CPAP Community, "what is wrong with me" [Web log post]. Retrieved from http://www.cpaptalk.com/viewtopic.
(Dec. 12, 2008), CPAP Community, "Any one tried a mask cover—gasket" [Web log post}. Retrieved from http://www.cpaptalk.com/viewtopic.
(2005), CPAP Community, "As long as I don't wake up" [Web log post}. Retrieved from http://www.cpaptalk.com/viewtopic.
International Search Report and Written Opinion for Application No. PCT/US2019/024220, dated Jul. 18, 2019, 11 pages.
International Preliminary Report on Patentability for PCT Application No. PCT/US2019/024220, dated Oct. 8, 2020, 8 pages.
Extended European Search Report for Application No. 19776419.4-1113, dated Dec. 10, 2021, 7 pages.

* cited by examiner

LINER AND RETAINING MEMBER FOR USE WITH RESPIRATORY MASK

CROSS-REFERENCE TO RELATED APPLICATIONS

This application claims the benefit of U.S. provisional application Ser. No. 62/648,895 filed Mar. 27, 2018, the disclosure of which is hereby incorporated in its entirety by reference herein.

TECHNICAL FIELD

Embodiments relate to a respiratory mask, a retaining member and liner for use with a respiratory mask, and combinations thereof.

BACKGROUND

A respirator is used to protect a user from inhaling dangerous substances, such as chemicals and particulate matter. A respirator typically includes a mask body for covering the user's nose and mouth, and one or more cartridges or canisters which include filters for removing the dangerous substances from the air inhaled by the user. Most respirator masks currently available are made from silicone, rubber, vinyl, or a nylon-based fabric. These materials are typically water and gas impermeable which can block off pores, cause sweating, and create pressure marks on the face, causing discomfort for the user. Since many users wear respirators for a significant part of each day, they need masks that are ergonomic and do not impose a physical burden even during periods of extended wear or environmental extremes such as high temperature and humidity.

Obstructive sleep apnea is a serious and potentially fatal medical condition in which a person's airway becomes physically blocked multiple times during sleep, restricting oxygen intake and causing the person to awake gasping for breath. Possible effects of the condition include extreme fatigue, high blood pressure, strokes, heart attacks, and sometimes even death. One of the most common treatments of obstructive sleep apnea is the use of a continuous positive airway pressure (CPAP) machine. These machines deliver a continuous flow of pressurized air to the airway through a hose and mask fitted to the face. Patient compliance is a major problem with CPAP users, however, due to discomfort, air leaks, and general ineffectiveness. It is estimated that up to 50% of users discontinue use.

As with respirators, most CPAP masks currently available are made from silicone, rubber, vinyl, or a nylon-based fabric. These materials are typically water and gas impermeable, which can block off pores, cause sweating, and create pressure marks on the face, increasing the discomfort of the mask. Furthermore, most mask manufacturers recommend against the use of skin or face cream with CPAP masks such the mask material directly contacts the skin. This is a problem for many users, especially those that have dry skin and depend on night cream for skin care.

SUMMARY

In one or more embodiments, a respiratory mask includes a mask body having a face-engaging portion. At least one retaining member is connected to the mask body, the at least one retaining member including at least one engaging member for receiving a liner and tethering the liner to the respiratory mask to generally overlie the face-engaging portion.

In one or more embodiments, a retaining member for use with a respiratory mask includes a flexible elongated body having a central portion and opposing ends on either side of the central portion, the body having a bottom surface arranged to be attached to the respiratory mask. At least one engaging member extends from the body for receiving a liner and tethering the liner to the respiratory mask.

In one or more embodiments, a liner for use with a respiratory mask having a face-engaging portion and a retaining member includes a liner body constructed from an absorbent material, the liner body having an outer edge, an inner edge, and an opening bounded by the inner edge. When the liner is positioned between the face-engaging portion and a face of a user, an extending portion of the liner body is defined which extends outwardly beyond the face-engaging portion, the extending portion including at least one aperture for engaging the retaining member to tether the liner to the respiratory mask.

In one or more embodiments, a kit for use with a respiratory mask includes at least one liner including a liner body constructed from an absorbent material, the liner body having an outer edge, an inner edge, and an opening bounded by the inner edge. The kit further includes at least one retaining member arranged to be connected to the respiratory mask, the at least one retaining member including at least one engaging member for receiving the liner and tethering the liner to the respiratory mask.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Embodiments disclosed herein provide a respiratory mask and accessories for use with a respiratory mask which are capable of improving the comfort, effectiveness, and/or user compliance of respiratory masks.

Figure 1:
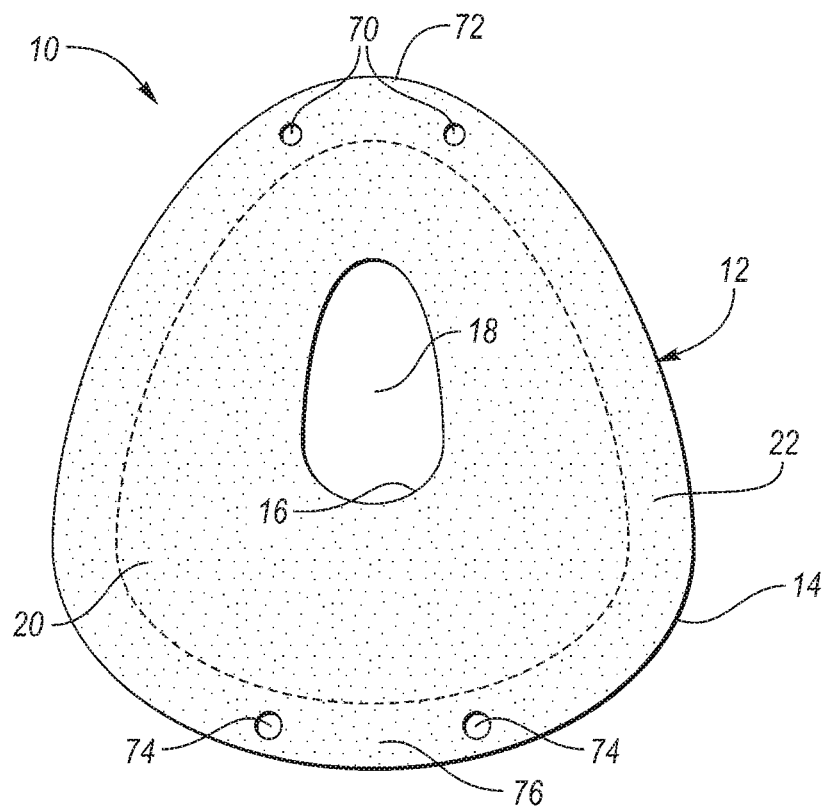
FIG. 1 is a top plan view of a liner according to an embodiment, such as for use with a respiratory mask.
Figure 2:
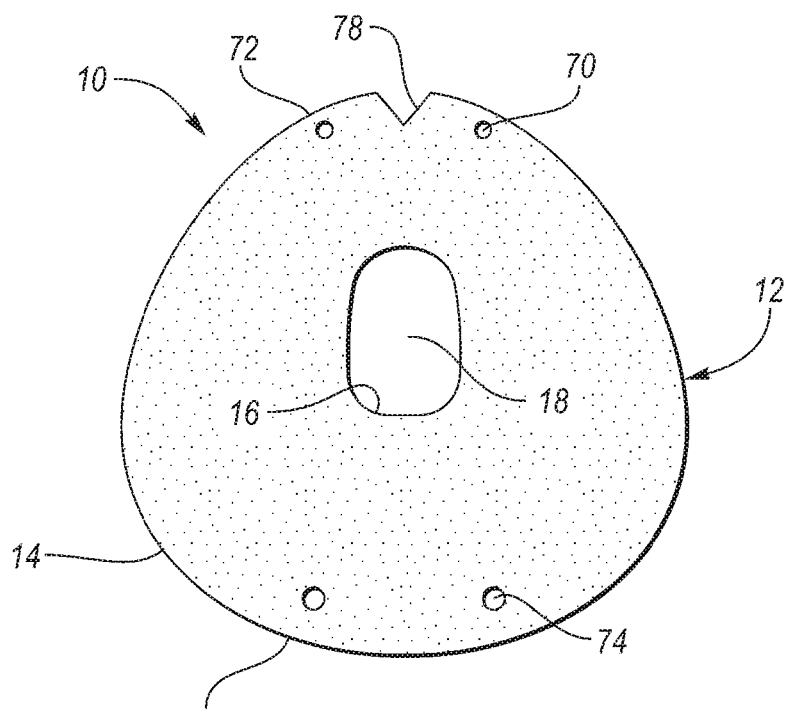
FIG. 2 is a top plan view of a liner according to another embodiment.
Figure 3:
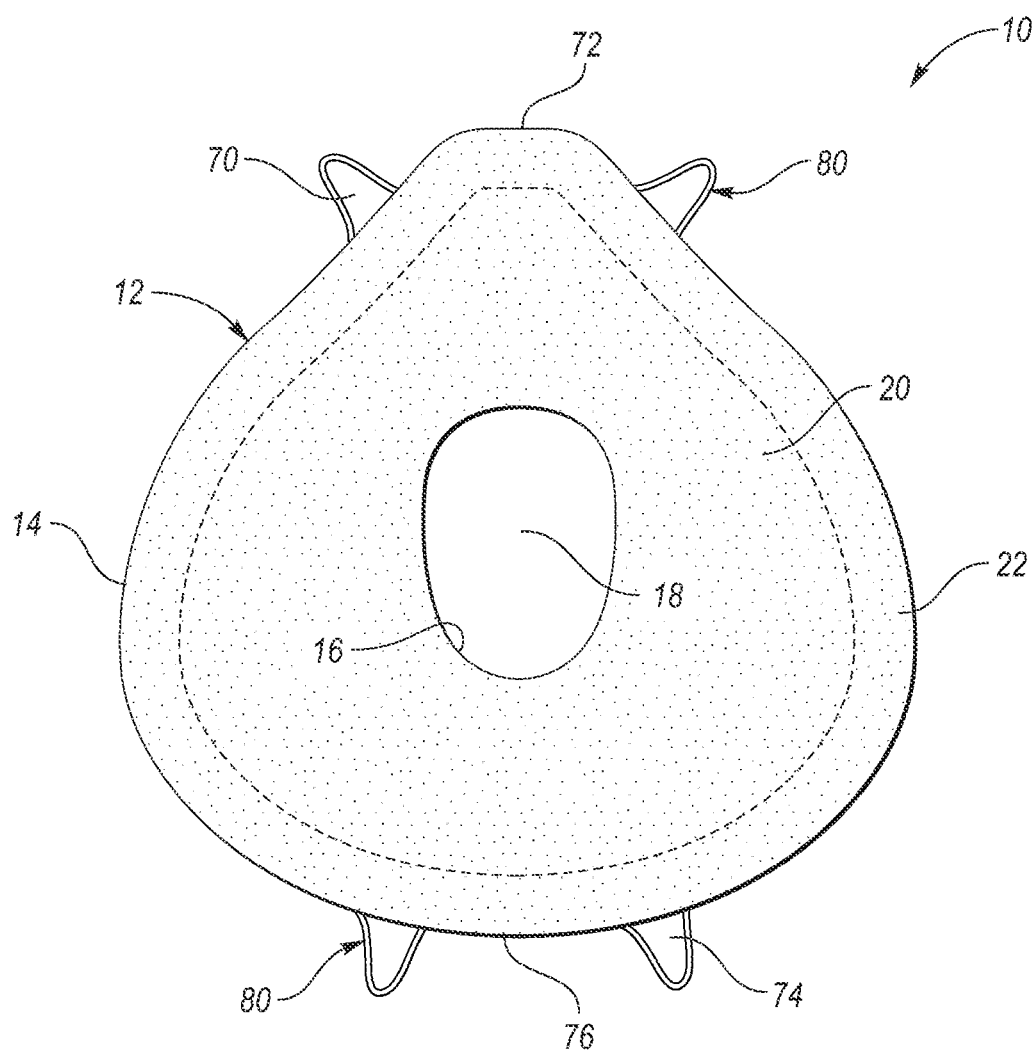
FIG. 3 is a top plan view of a liner according to yet another embodiment.

With reference to FIGS. 1-3, a liner for use with a respiratory mask, such as a respirator 100 (see FIGS. 6-12), is illustrated and designated generally by reference numeral 10. In use, the liner 10 may be positioned between the respiratory mask and the face of a user, such as to absorb moisture, maintain proper positioning of the respiratory mask, and to greatly reduce or eliminate air from leaking between the respiratory mask and the user's face. Although the liner 10 is described herein primarily in relation to use with a respirator 100, it is understood that the liner 10 is not limited to use with respirators, and that the description provided herein is equally applicable to use of the liner 10 with other types of respiratory masks such as, but not limited to, CPAP masks 200 (see FIG. 13) or oxygen masks 300 (see FIG. 14).

In one embodiment, the liner 10 includes a liner body 12 having an outer edge 14, an inner edge 16, and an opening 18 bounded by the inner edge 16. The liner body 12 may be generally oval-shaped, elliptical, round, or triangular, or have any other shape appropriate for use with a respiratory mask and is not limited to the shapes depicted herein. The opening 18 is designed to at least partially receive the nose, mouth, or both nose and mouth, depending upon the type of respiratory mask. The opening 18 may be generally elliptical or oval-shaped as shown, but is not intended to be limited to these shapes.

Figure 4:
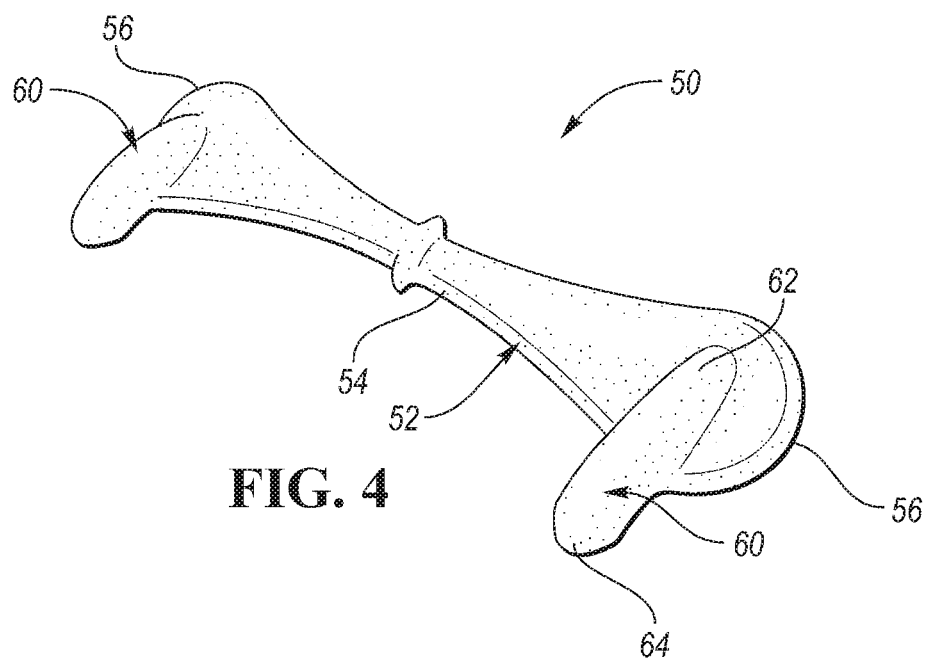
FIG. 4 is a perspective view of a retaining member according to an embodiment.
Figure 5:
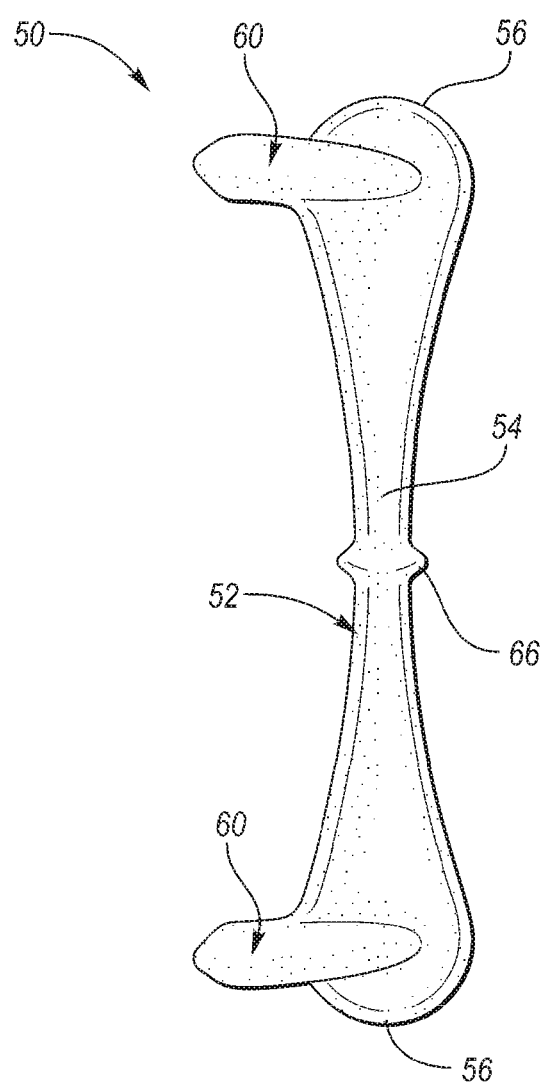
FIG. 5 is a top plan view of the retaining member.
Figure 6:
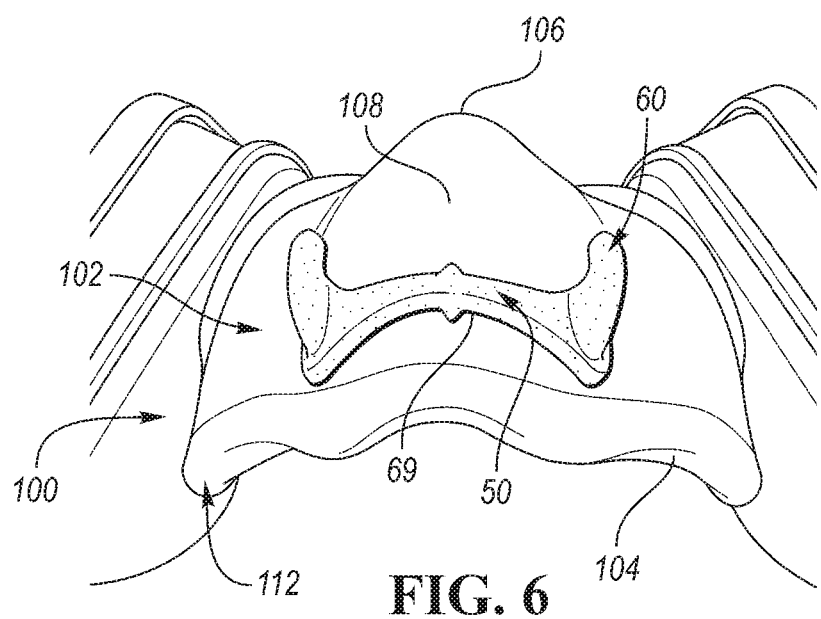
FIG. 6 is a top perspective view of the retaining member connected to a top side of a respirator.
Figure 7:
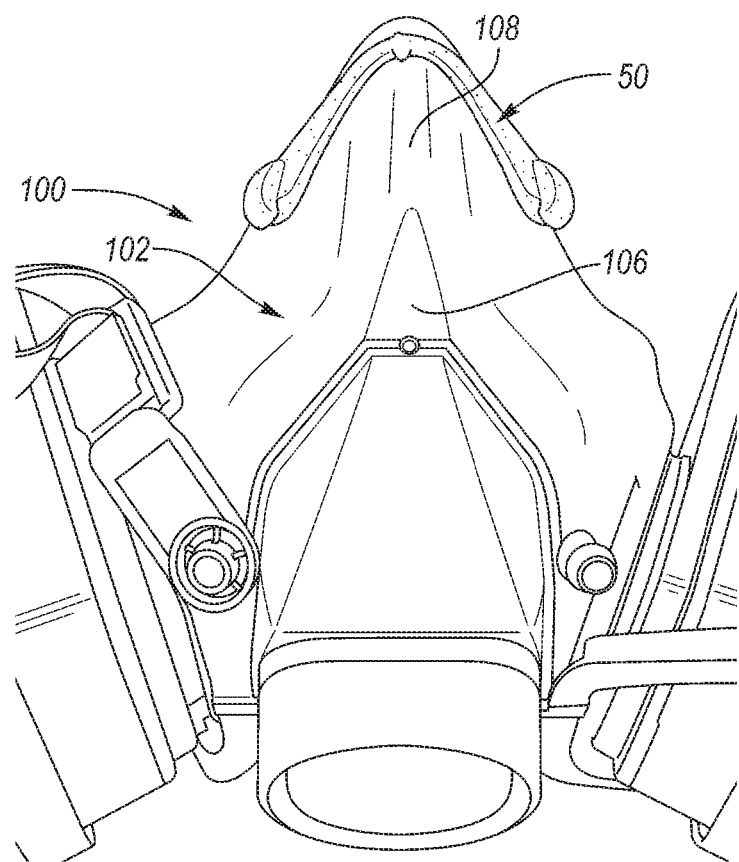
FIG. 7 is a rear view of the retaining member connected to the top side of a respirator.
Figure 8:
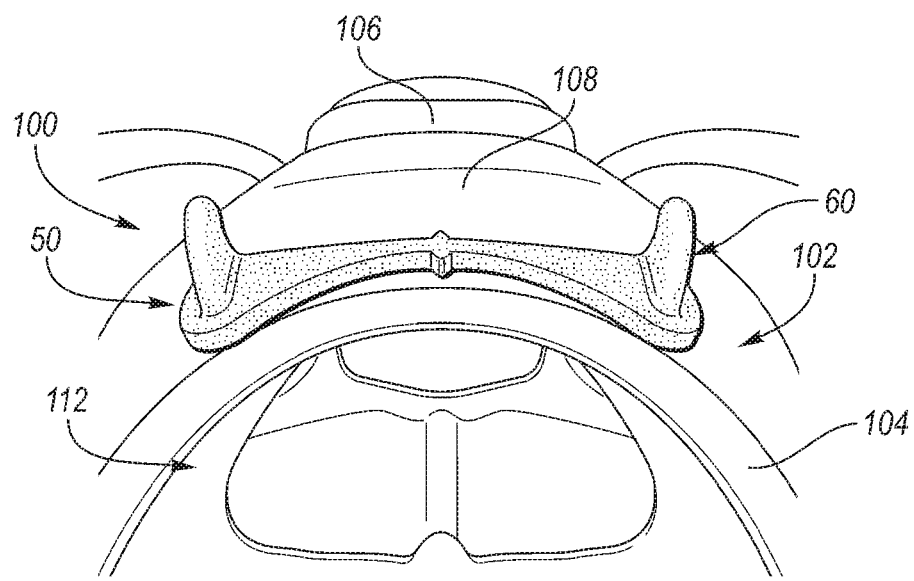
FIG. 8 is front perspective view of the retaining member connected to the top side of a respirator.
Figure 9:
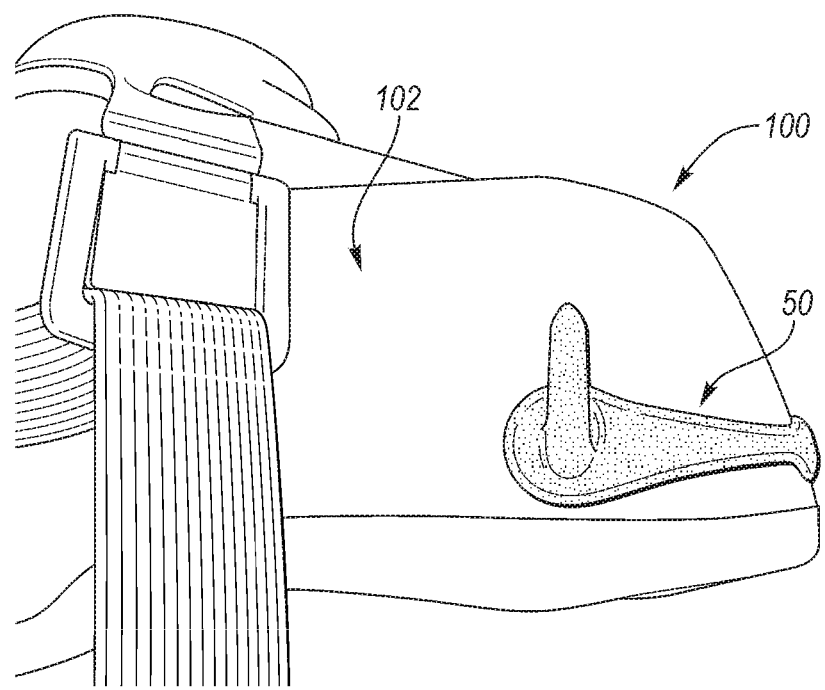
FIG. 9 is a side view of the retaining member connected to a respirator.

With reference now to FIGS. 4 and 5, a retaining member 50 can be connected to the respiratory mask and provided to receive and engage the liner 10, allowing the liner 10 to be tethered to the respiratory mask and to be retained in a desired position with respect to the respiratory mask. The retaining member 50 includes a body, which in one embodiment may be an elongated body 52 having a central portion 54 and opposing ends 56 on either side of the central portion 54. The retaining member 50 further includes at least one engaging member, which in one embodiment may include a post or hook 60 having a proximal end 62 and a distal end 64, where one hook 60 may be provided at or near each end 56 of the body 52. The retaining member 50 and included hooks 60 may be constructed from any suitably flexible and durable material, such as a plastic or rubber material. Resilience of the retaining member 50 and hooks 60 may be advantageous in conforming the elongated body 52 to the respiratory mask, engaging and retaining the liner 10, and preventing damage of the retaining member 50 in the event that an external force is applied to the retaining member 50 during use of the respiratory mask. As shown, the central portion 54 of the body 52 may be narrower than the ends 56, which may also facilitate flexibility of the retaining member 50. The central portion 54 may also include a marker 66 identifying a center of the body 52 for facilitating alignment and symmetrical placement on the respiratory mask. Although an elongated body 52 is shown herein, the body 52 is not limited to this configuration, and it is contemplated that the body 52 could alternatively have other shapes with one or more engaging members extending therefrom.

Figure 15:
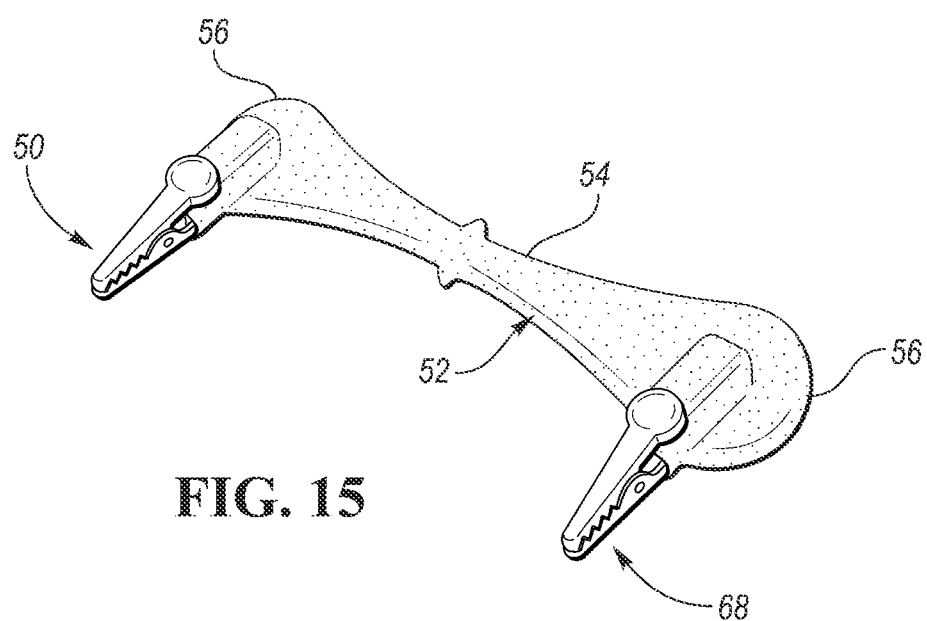
FIG. 15 is a perspective view of a retaining member according to another embodiment.

In one embodiment, each hook 60 extends upwardly from the body 52 at its proximal end 62, and then extends outwardly or laterally with respect to the body 52 to terminate in the distal end 64, where the distal end 64 may extend beyond the body 52. The hooks 60 may have rounded distal ends 64 and may have narrower distal ends 64 compared with the proximal ends 62, both of which may facilitate receiving and retaining the liner 10 on the retaining member 50. Of course, the retaining member 50 and the hooks 60 are not limited to the configuration shown and described herein. For example, instead of two spaced hooks 60, it is contemplated that only one hook or more than two hooks could be provided. In addition, the post or hook 60 may have a different configuration, such as extending upwardly from the body 52 and having a narrower proximal end 62 compared with the distal end 64. The retaining member 50 may alternatively include another type of engaging member altogether, such as a clip 68 (e.g., hinged, spring-loaded, alligator, etc.) or the like as illustrated in FIG. 15.

As shown in FIGS. 1 and 2, the liner 10 may have one or more apertures sized to be received by the hooks 60 for tethering the liner 10 to the respiratory mask and retaining a desired position of the liner 10. In the illustrated embodiment, a first or top pair of spaced apertures 70 may be adjacent a first end 72 of the liner 10, and a second or bottom pair of spaced apertures 74 may be adjacent a second end 76 of the liner 10. The first and second pairs of apertures 70, 74 may be generally circular or oval-shaped as shown, but are not intended to be limited to these shapes. The configuration of the apertures 70, 74 can be designed to correspond to the configuration of the hooks 60 and the retaining member 50. As such, although a pair of apertures 70, 74 is shown at each end 72, 76 of the liner 10, the liner 10 is not limited to this embodiment. Alternatively, for example, apertures may be provided on only one end 72, 76 of the liner 10, or a single aperture or more than two apertures may be provided at one or both ends 72, 76 or on other portions of the liner 10.

Turning to FIGS. 6-9, the retaining member 50 may be connected to a respiratory mask, such as a respirator 100, having a mask body 102 with a front side 104, a rear side 106, a top side 108, and a bottom side 110. As shown, in one embodiment the hooks 60 may be oriented toward the rear side 106 of the respiratory mask, away from a face-engaging portion 112 on the front side 104. The retaining member 50 can be affixed to the respiratory mask by any method, such as with an adhesive or with a hook and loop material to join a bottom surface 69 of the retaining member 50 to the mask body 102. The retaining member 50 can be removably attached to the mask body 102 so that it can be repositioned or removed if necessary. Alternatively, the retaining member 50 could be integrally formed with the mask body 102 during manufacturing, such as via injection molding. In another embodiment, a kit including one or more liners 10 and retaining members 50 could be provided for use in retrofitting a respirator 100, CPAP mask 200, oxygen mask 300, or other respiratory mask.

Figure 10:
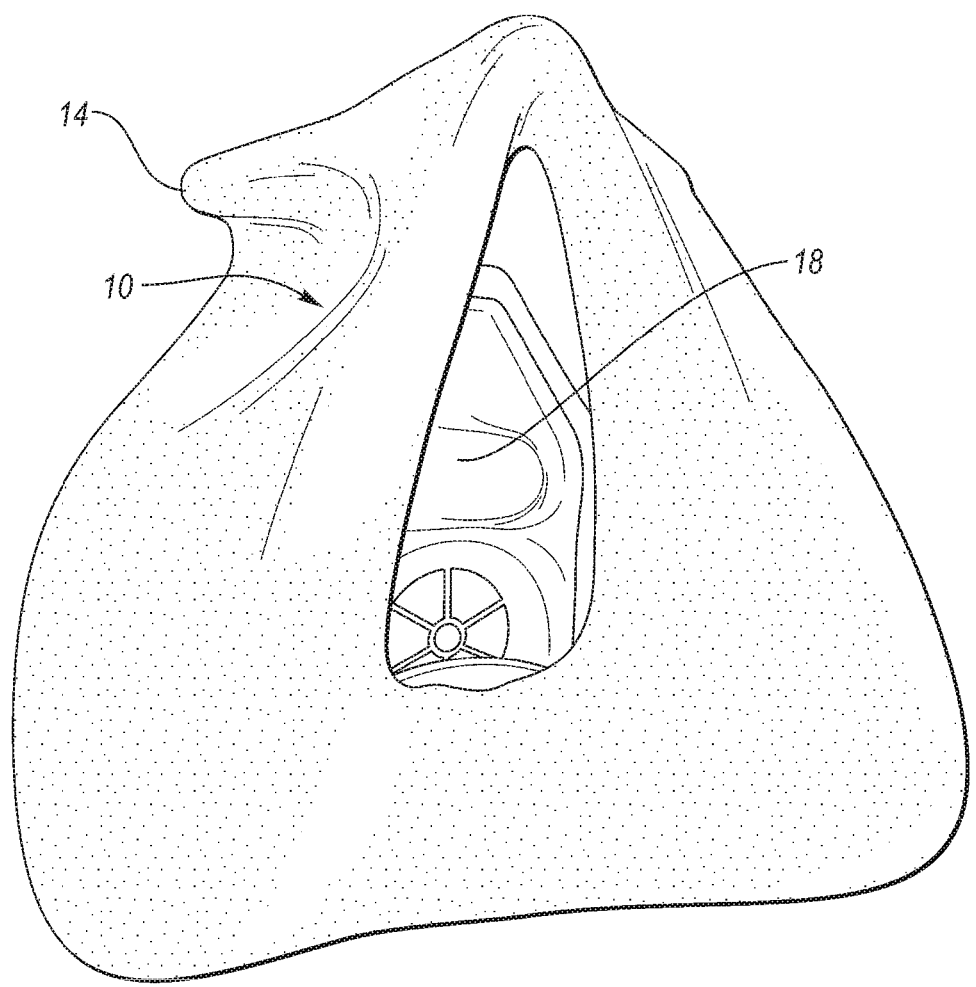
FIG. 10 illustrates a liner retained on a respirator.
Figure 11:
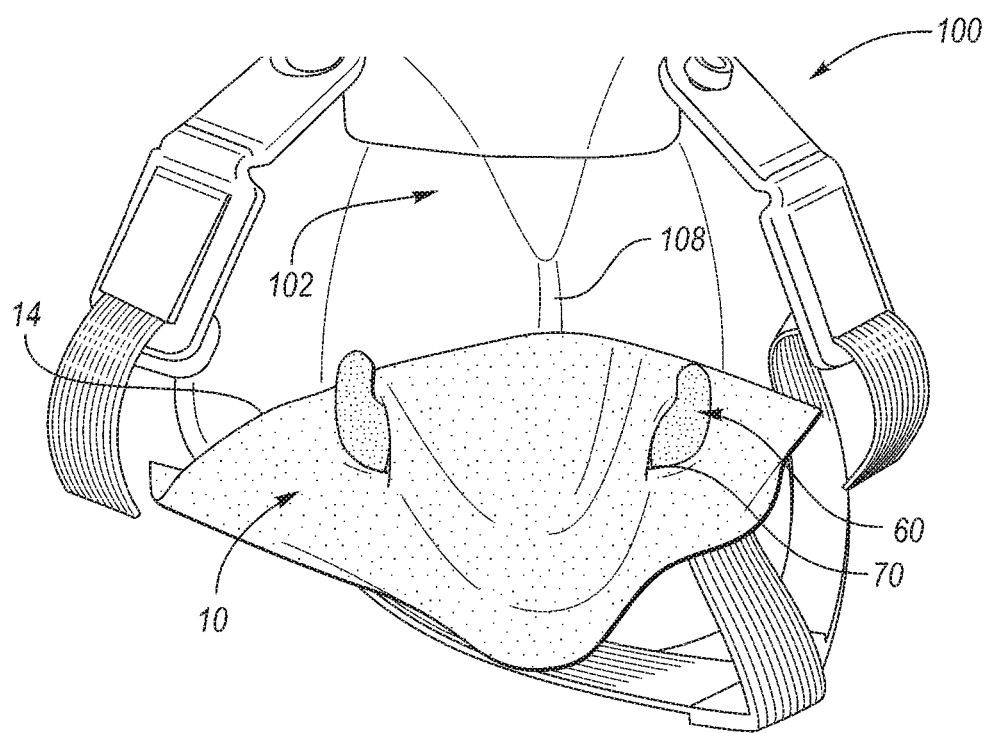
FIG. 11 is a top view of the liner engaged by the hooks of a retaining member on the top side of a respirator.
Figure 12:
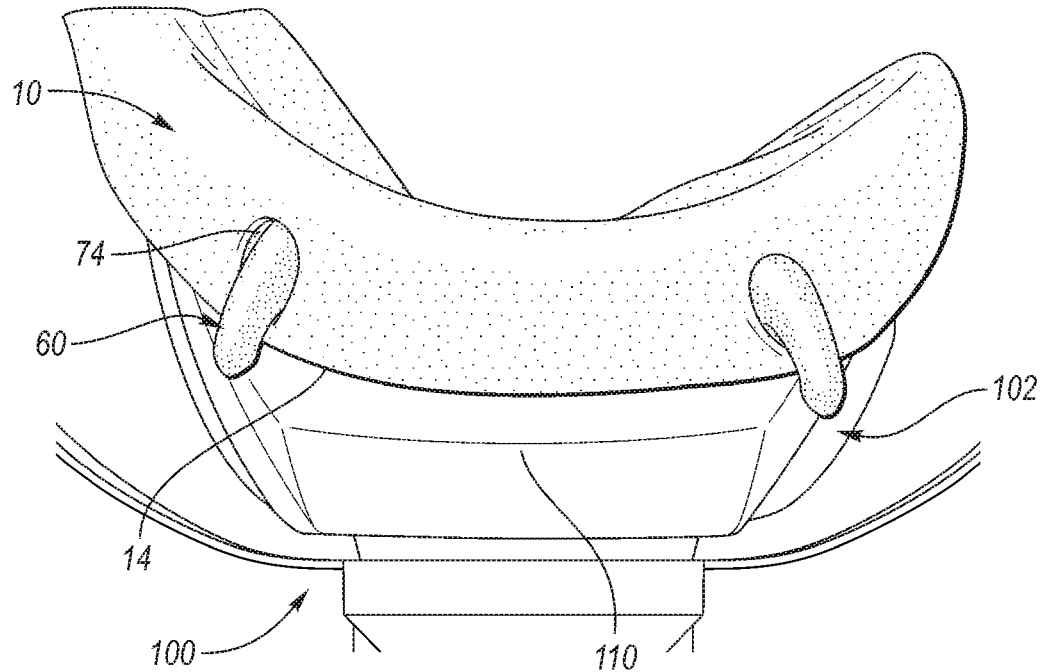
FIG. 12 is a bottom view of the liner engaged by the hooks of a retaining member on a bottom side of a respirator.

FIGS. 10-12 depict a liner 10 tethered to a respirator 100 via one or more retaining members 50. FIG. 10 illustrates alignment of the opening 18 with the face-engaging portion 112, wherein retaining members 50 can be positioned on the mask body 102 with placements that engage and properly align the liner 10 to generally overlie the face-engaging portion 112. FIG. 11 illustrates engagement of the first pair of apertures 70 with a retaining member 50 on the top side 108 of the respirator 100, and FIG. 12 illustrates engagement of the second pair of apertures 74 with a retaining member 50 on the bottom side 110 of the respirator 100, such that the liner 10 is retained in a desired position with respect to the respirator 100. While retaining members 50 are shown positioned on the top and bottom sides 108, 110 of the mask body 102, it is understood that retaining members 50 could additionally or alternatively be positioned on the side or other regions of the respiratory mask and corresponding apertures formed in different portions of the liner 10.

Figure 13:
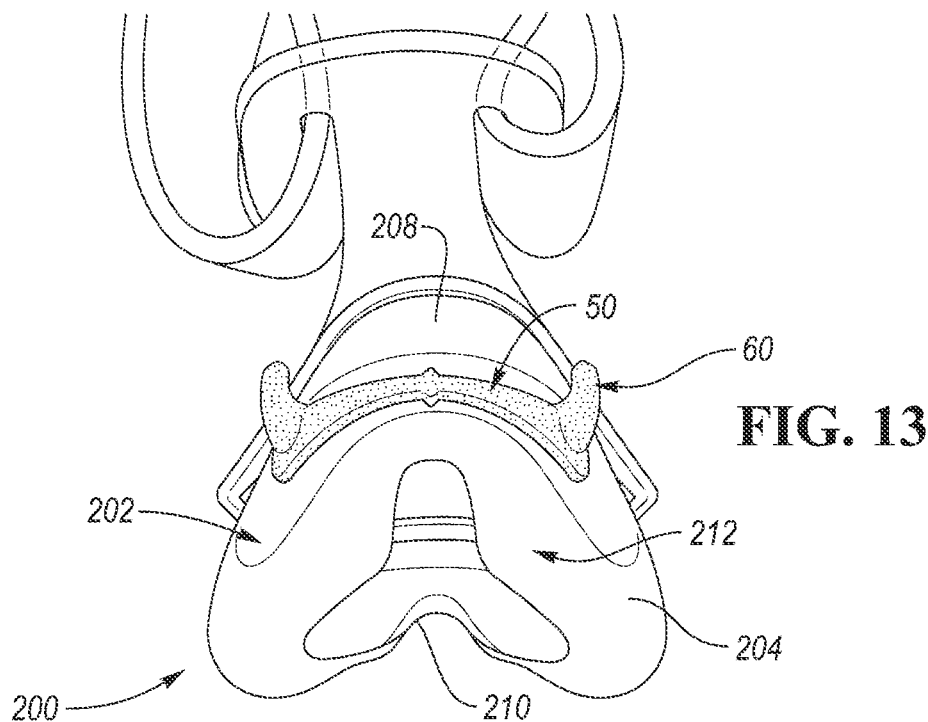
FIG. 13 is a top perspective view of a retaining member on a CPAP mask.
Figure 14:
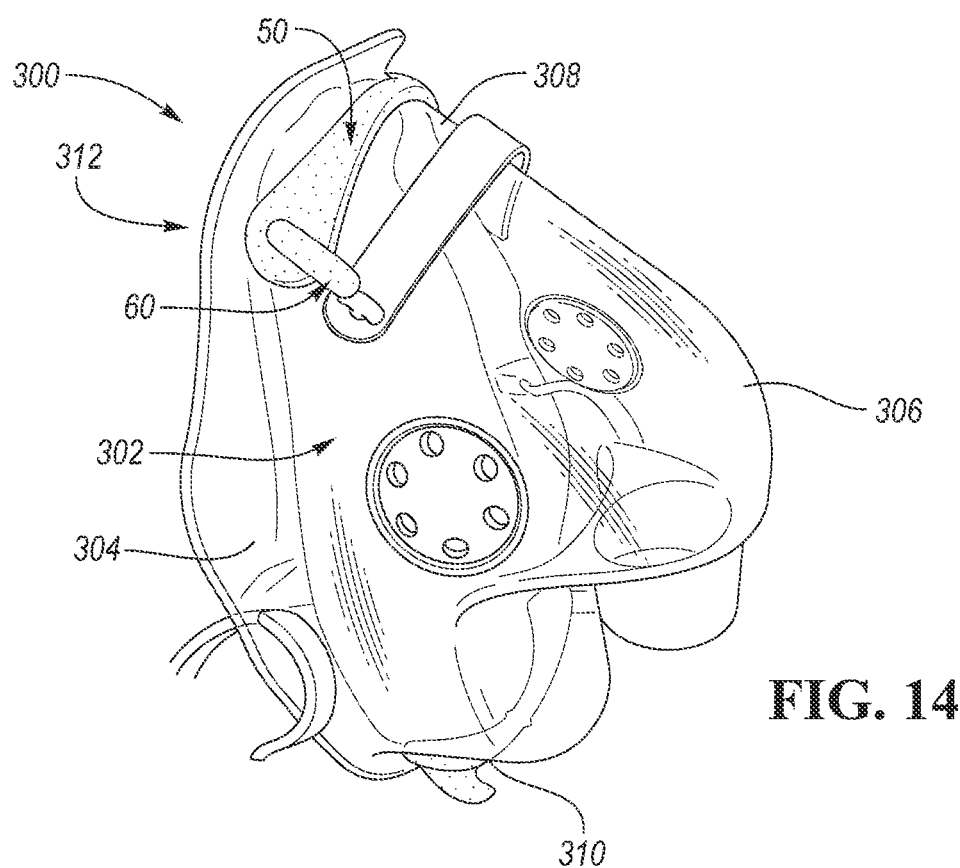
FIG. 14 is perspective view of a retaining member on an oxygen mask.

The features of respirator 100 described above with reference to FIGS. 6-12 may also be applicable to the CPAP mask 200 shown in FIG. 13 and the oxygen mask 300 shown in FIG. 14, wherein the respiratory mask features described for respirator 100 are given like reference numerals with the substitution of a "2" prefix for the CPAP mask 200 and with the substitution of a "3" prefix for the oxygen mask 300.

The outer edge 14 of liner 10 may have a shape scaled to a general shape of the face-engaging portion 112, 212, 312 (see, for example, FIGS. 8 and 13-14) of the respiratory mask 100, 200, 300. As best shown in FIG. 10, a perimeter of the liner outer edge 14, which may be continuous or discontinuous, is larger than a perimeter of the face-engaging portion 112, wherein the outer edge 14 extends outwardly beyond the face-engaging portion 112 around at least part of the perimeter of the face-engaging portion 112. As such, as illustrated in an exemplary manner in FIGS. 1 and 3 by the broken line, the liner body 12 has a first portion 20 which will be disposed inward of the perimeter of the face-engaging portion 112 when the liner 10 is tethered to the respiratory mask, and a second, extending portion 22 which will be disposed outward of the perimeter of the face-engaging portion 112 in a freely extendible manner when the liner 10 is tethered to the respiratory mask. In general, the area of the extending portion 22 may comprise at least about 5%, 10%, or 15% of the area of the liner body 12, but larger proportions of area represented by the extending portion 22 are also contemplated.

Once the liner 10 is engaged by the retaining member 50 on the respiratory mask 100, 200, 300, the user may fit his/her nose and/or mouth (as applicable) into the opening 18 and secure the respiratory mask to his/her head, such as with straps. Securing the respiratory mask releasably holds the liner 10 between the face-engaging portion 112, 212, 312 and a user's face, such that the liner 10 may regulate air flow and reduce air leaks between the face-engaging portion and the user's face. The liner 10 may be adjusted if necessary, such as around the nose and mouth, by pulling outward on the protruding extending portion 22 while the respiratory mask is secured, thereby providing a customized fit for a particular user. The liner 10 is held in place by the retaining member 50 as well as the pressure of the respiratory mask upon the user's face, and the liner 10 is easily removable and replaceable when the respiratory mask is removed. The outer edge 14 and extending portion 22 will extend outwardly from the face-engaging portion 112, 212, 312 and may generally follow the contours of the user's face. The outer edge 14 of the liner 10 loosely protrudes beyond the face-engaging portion such that the extending portion 22 may be in non-adhering, non-sealing communication with a user's face. In this manner, the liner 10 and its extending portion 22 may serve to reduce air leaks from the perimeter of the face-engaging portion by acting as a baffle to regulate, limit, or diffuse air flow between the respiratory mask and the skin.

During use, it may be necessary for the user to remove the respiratory mask temporarily. For example, a user may wish to remove a respirator 100 in certain instances, such as to have a conversation with a coworker, to drink or eat, or to take a break during a job. A CPAP user may wish to remove his/her CPAP mask 200 while in use, such as during the night to use the restroom or to get a drink of water. In a hospital or home setting, a user may need to have an oxygen mask 300 removed for a temporary period, such as to eat, drink, or take medication. According to the embodiments disclosed herein, when the user removes the respiratory mask, the liner 10 is retained in position on the respiratory mask by the retaining member 50. Accordingly, if a user needs to remove the respiratory mask for any reason, the user will not have to reposition or replace the liner 10 when he/she puts the respiratory mask on again. When the user does wish to replace the liner 10, the liner 10 is disposable and may be easily removed from the retaining member 50, discarded, and then replaced with another liner 10. Advantageously, use of the liner 10 prevents direct skin contact with the mask material, decreasing the need to clean the respiratory mask as frequently.

Since the apertures 70, 74 may be provided in the extending portion 22 of the liner 10, the apertures 70, 74 do not alter the function of the liner 10 or its interface with the face-engaging portion 112, 212, 312. As such, the liner 10 described herein can be used with a respiratory mask whether or not a retaining member 50 is associated with the respiratory mask or whether or not engagement of the liner 10 with a retaining member 50 is utilized. The apertures 70, 74 do not increase the overall footprint of the liner 10, and do not require the liner 10 to be manufactured with auxiliary attachment members. However, alternative embodiments are also contemplated where instead of or in addition to having apertures 70, 74 in the extending portion 22 set inwardly from the liner outer edge 14, the extending portion 22 may include loops or tabs 80 which extend outwardly from the liner outer edge 14 and include apertures 70, 74 as illustrated in FIG. 3. Still further, such tabs/loops 80 or other portions of the liner 10 could include adhesive for removably affixing the liner 10 to part of the respiratory mask. In an embodiment where the engaging member includes a clip-type structure instead of a hook 60, a liner 10 without apertures 70, 72 could be utilized.

According to an embodiment, the liner body 12 may be constructed from a single layer of absorbent material, wherein the thickness of the liner body 12 may be between about 0.005 to 0.05 inches, although these dimensions are not intended to be limiting. In one embodiment, the material may include cotton. In another embodiment, the material may include another material, such as silicone, with cotton embedded therein. However, it is understood that any material with suitable absorption and comfort properties may be used. In further accordance with an embodiment, the material used for the construction of the liner body 12 may be stretchable to aid in adjusting and customizing the fit of the liner 10 to a particular user as described above. The liner 10 may also include a notch 78 or indented section at one end 72 thereof to correspond with the nose region of a user, which may provide a more unobstructed line of sight for the user when the liner 10 is retained in position on the respiratory mask.

Copper is a natural mineral having human nutritional benefit. Copper is also known to provide antimicrobial and potential wound healing properties. In one embodiment, the liner described herein may be manufactured with a copper or copper oxide material, such as CUPRON®.

Due to the moisture content of the air, facial perspiration (such as due to contact with the mask material), and oil from the skin, the respiratory mask 100, 200, 300 may slip on the user's face, thus leaking air. The absorbent material of the liner 10 may function to absorb moisture and/or oils from the user's skin and wick it away from the face and the face-engaging portion 112, 212, 312, enabling the respiratory mask to maintain a consistent and comfortable position with respect to the user's face when in use. As a result, proper positioning of the face-engaging portion with respect to the user's skin may be maintained, thus eliminating or greatly reducing air leaks and facilitating the ability for a user to wear their respiratory mask more comfortably.

The single layer construction of the liner 10 may act as a sort of "second skin" upon the user's face. As such, the liner 10 is able to provide its functions without detracting from the prescribed fit of the respiratory mask 100, 200, 300 since the liner 10 does not appreciably alter the distance of the face-engaging portion 112, 212, 312 from the user's face. Pressure markings from the face-engaging portion on a user's face may also be reduced or eliminated by use of the liner 10. Furthermore, the absorbent liner material may make use of facial creams possible while wearing a respiratory mask, since direct contact of the skin with the mask material is avoided.

Respiratory masks are offered in various shapes and sizes, including full-face, nasal, child-sized, and partial-face (hybrid) configurations. Full-face masks typically include a wider bottom region for covering the mouth area and a narrower upper region for covering the nasal area. Nasal masks generally cover the nasal area and not the mouth area. Child-sized masks may have a proportionally smaller size. Partial-face (hybrid) masks generally cover the mouth and may include a nasal interface. It is therefore contemplated that the outer edge 14 of liner 10 may have a shape similar to a general shape of the face-engaging portion for a selected respiratory mask, wherein the shape of the outer edge 14 may represent a scaled version of the general shape of the face-engaging portion.

The liner 10 and the retaining member 50 disclosed herein may facilitate a more comfortable and effective mask-wearing experience for the user by contributing to a good fit of a respiratory mask, providing comfort to the user, eliminating moisture, and reducing or eliminating air leaks. Furthermore, tethering the liner 10 to the respiratory mask via the retaining member 50 makes it easy to remove the respiratory mask temporarily and then secure the mask at a later time without having to reposition or replace the liner 10.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A respiratory mask, comprising:
   a mask body having a face-engaging portion; and
   at least one retaining member connected to the mask body, the at least one retaining member including a flexible elongated body and at least one engaging member, the flexible elongated body having a central portion and opposing ends on either side of the central portion, wherein the central portion is narrower than the opposing ends, the at least one engaging member extending upwardly from the flexible elongated body and configured for receiving a liner and tethering the liner to the respiratory mask to generally overlie the face-engaging portion.

2. The respiratory mask of claim 1, wherein the at least one retaining member is removably attached to the mask body.

3. The respiratory mask of claim 1, wherein the at least one retaining member is integrally formed with the mask body.

4. The respiratory mask of claim 1, wherein the at least one engaging member includes a hook.

5. The respiratory mask of claim 1, wherein the at least one engaging member includes a clip.

6. A retaining member for use with a respiratory mask, the retaining member comprising:
   a flexible elongated body having a central portion and opposing ends on either side of the central portion, wherein the central portion is narrower than the opposing ends, the flexible elongated body having a bottom surface arranged to be attached to the respiratory mask; and
   at least one engaging member extending upwardly from the flexible elongated body and configured for receiving a liner and tethering the liner to the respiratory mask.

7. The retaining member of claim 6, wherein the at least one engaging member includes at least one hook.

8. The retaining member of claim 6, wherein the at least one engaging member includes at least one clip.

9. The retaining member of claim 6, wherein the at least one engaging member includes an engaging member provided at each of the opposing ends of the flexible elongated body.

10. The retaining member of claim 6, wherein the central portion includes a marker for identifying a center of the body.

11. A kit for use with a respiratory mask, comprising:
    at least one liner including a liner body constructed from an absorbent material, the liner body having an outer edge, an inner edge, and an opening bounded by the inner edge; and
    at least one retaining member arranged to be connected to the respiratory mask, the at least one retaining member including a flexible elongated body and at least one engaging member, the at least one engaging member extending upwardly from the flexible elongated body and configured for receiving the liner and tethering the liner to the respiratory mask,
    wherein the liner body includes at least one aperture arranged to be received by the at least one engaging member.

12. The kit of claim 11, wherein the at least one engaging member includes a hook.

13. The kit of claim 11, wherein the at least one engaging member includes a clip.

14. The kit of claim 11, wherein the at least one aperture includes a first pair of spaced apertures adjacent a first end of the liner.

15. The kit of claim 11, wherein the at least one aperture includes a first pair of spaced apertures adjacent a first end of the liner and a second pair of spaced apertures adjacent a second end of the liner.

16. The kit of claim 11, wherein the liner includes at least one tab extending outwardly from the outer edge of the liner body.

17. The kit of claim 16, wherein at least one aperture is provided in the at least one tab.

18. The kit of claim 11, wherein the liner body includes a notch at one end thereof.

\* \* \* \* \*